United States Patent [19]

Gewartowski et al.

[11] 4,381,418
[45] Apr. 26, 1983

[54] CATALYTIC DEHYDROGENATION PROCESS

[75] Inventors: Steve A. Gewartowski, Mt. Prospect; Dennis E. O'Brien, Arlington Heights, both of Ill.

[73] Assignee: UOP Inc., Des Plaines, Ill.

[21] Appl. No.: 327,656

[22] Filed: Dec. 4, 1981

[51] Int. Cl.³ .............................................. C07C 5/36
[52] U.S. Cl. .................................... 585/655; 585/654; 62/23; 62/24; 62/27
[58] Field of Search ................... 62/11, 23, 24, 27, 28; 585/654, 655

[56] References Cited

U.S. PATENT DOCUMENTS

| | | | |
|---|---|---|---|
| 2,620,314 | 12/1952 | Hoekstra | 252/448 |
| 3,119,677 | 1/1961 | Moon et al. | 62/28 |
| 3,647,680 | 3/1972 | Greenwood et al. | 208/65 |
| 4,257,794 | 3/1981 | Shirokov et al. | 62/23 |
| 4,272,270 | 6/1981 | Higgins | 62/24 |
| 4,343,633 | 8/1982 | Kick et al. | 62/23 |

FOREIGN PATENT DOCUMENTS

| | | | |
|---|---|---|---|
| 1041003 | 6/1976 | Canada | 62/24 |
| 51-3028565 | 8/1976 | Japan | 62/11 |

OTHER PUBLICATIONS

Berg et al., Oil and Gas Journal, Nov. 10, 1980, pp. 191-197.

*Primary Examiner*—Delbert E. Gantz
*Assistant Examiner*—A. Pal
*Attorney, Agent, or Firm*—James R. Hoatson, Jr.; Robert W. Welch; William H. Page, II

[57] ABSTRACT

A process for the catalytic dehydrogenation of $C_2+$ normally gaseous paraffinic hydrocarbons to produce the corresponding monoolefinic hydrocarbons is disclosed. The energy-efficient process is particularly directed to the separation of recycle hydrogen from the olefinic hydrocarbon products and unreacted paraffinic hydrocarbons.

9 Claims, 1 Drawing Figure

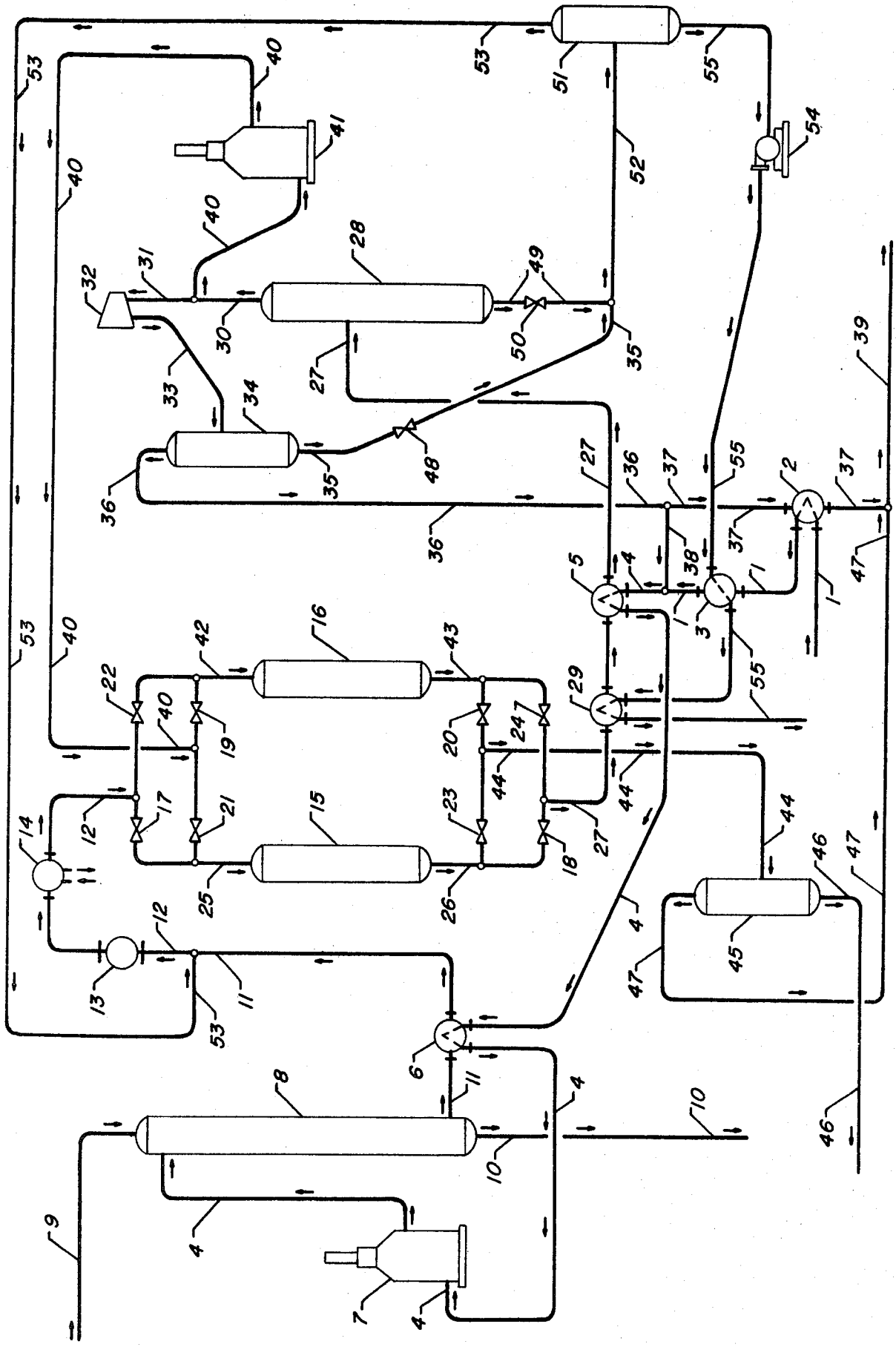

CATALYTIC DEHYDROGENATION PROCESS

This invention relates to a process for the catalytic dehydrogenation of $C_2+$ normally gaseous paraffinic hydrocarbons to produce low molecular weight, normally gaseous monoolefinic hydrocarbons—an established and well known hydrocarbon conversion process in the petroleum refining industry. The monoolefinic hydrocarbon products are generally useful as intermediates in the production of other more valuable hydrocarbon conversion products, and the catalytic dehydrogenation process is typically utilized in conjunction with various other hydrocarbon conversion processes to yield a desired final product. For example, utilizing liquid petroleum gas (LPG)—a compressed or liquefied gas consisting of propane and butane or mixed butanes derived as a by-product of petroleum refining—as a starting material, catalytic dehydrogenation can be utilized to produce propylene and/or butylenes in conjunction with an HF alkylation unit wherein said olefins are alkylated with isobutane to produce a high octane motor fuel; or in conjunction with a catalytic condensation unit wherein said olefins are condensed to form tetramers or polymer gasoline; or in conjunction with an etherification unit wherein isobutylene is reacted with methanol to produce methyl t-butyl ether, a highly desirable gasoline additive.

Notwithstanding that certain of the catalyzed hydrocarbon conversion process, including the dehydrogenation process herein contemplated, involve hydrogen-producing reactions, it has been the practice to charge hydrogen to the reaction zone in admixture with the hydrocarbon feedstock. This practice has been found to promote catalyst activity as well as activity stability. The hydrogen admixed with the hydrocarbon feedstock is almost invariably recycle hydrogen separated as a hydrogen-rich vapor phase from the reaction zone effluent. Hydrogen in excess of that required for recycle purposes is recovered as net hydrogen and utilized in other processes integrated into the overall petroleum refining operation.

The separation of a hydrogen-rich vapor phase from a reaction zone effluent stream is a common practice. In those hydrocarbon conversion processes wherein the reaction zone effluent consists largely of normally liquid hydrocarbons and hydrogen, a suitable separation is generally accomplished by condensing out said hydrocarbons in a gas-liquid separator at relatively mild conditions of temperature and pressure. The further purification of the hydrogen-rich vapor phase can be accomplished, if so desired, at more severe conditions of temperature and pressure, but said purification will involve the treatment of substantially less than the total reaction zone effluent. In contrast, when the reaction zone effluent consists largely of normally gaseous hydrocarbons and hydrogen, as is the case with the catalytic dehydrogenation process herein contemplated, the separation of a vapor phase suitably rich in hydrogen requires treatment of the total reaction zone effluent at the more severe conditions of temperature and pressure entailing an increased use of utilities.

In the latter case, the problem is further compounded with respect to the dehydrogenation of $C_3$–$C_4$ paraffinic hydrocarbons to produce the corresponding monoolefins. Equilibrium conditions relating to the dehydrogenation reaction limit conversions to from about 30 to about 50 mol.% at optimum conditions of temperature and pressure. It follows tht the overall conversion will be reduced in proportion to the amount of olefinic product returned to the dehydrogenation zone in admixture with the recycle hydrogen. It is therefore imperative that in the separation of the normally gaseous hydrocarbons from the recycle hydrogen, substantially all of the olefinic product must be separated to assure an optimum conversion.

It is an object of this invention to present an improved process for the catalytic dehydrogenation of normally gaseous paraffinic hydrocarbons. It is a more specific object of this invention to provide an energy-efficient process for the separation of a hydrogen-rich vapor phase from a reaction zone effluent resulting from the catalytic dehydrogenation of normally gaseous paraffinic hydrocarbons.

In one of its broad aspects, the present invention embodies a catalytic dehydrogenation process which comprises the steps of (a) heat exchanging a $C_2+$ normally gaseous paraffinic hydrocarbon feed stream with a net hydrogen product stream and a net hydrocarbon product stream chilled in accordance with step (g); (b) further cooling said hydrocarbon feed stream on combination with a hydrogen recycle stream chilled in accordance with step (g) and recycled in accordance with step (h); (c) heating the combined hydrogen/hydrocarbon stream by indirect heat exchange with a reaction zone effluent stream compressed in accordance with step (e); (d) contacting the heated combined stream with a dehydrogenation catalyst in a reaction zone at dehydrogenation conditions producing a reaction zone effluent stream comprising hydrogen, olefinic hydrocarbon product and unreacted paraffinic hydrocarbons; (e) compressing said effluent stream and cooling the same on indirect heat exchange with the combined stream in accordance with step (c) and forming a liquid hydrocarbon phase and a hydrogen-rich vapor phase; (f) separating the thus cooled liquid hydrocarbon phase; (g) expanding the hydrogen-rich vapor phase to effect a further chilling and condensation of a residual hydrocarbon phase therefrom; (h) combining one portion of the chilled vapor phase with the hydrocarbon feed stream as recycle hydrogen in accordance with step (b); (i) heat exchanging the remaining portion of the chilled hydrogen-rich vapor phase with the hydrocarbon feed stream in accordance with step (a) and thereafter recovering said vapor phase as a net hydrogen product stream; (j) combining the cooled liquid hydrocarbon phase from step (f) and the chilled residual hydrocarbon phase from step (g), heat exchanging the combined hydrocarbon stream with the hydrocarbon feed stream in accordance with step (a), and thereafter recovering the combined stream as a net hydrocarbon products stream comprising olefinic hydrocarbon products stream comprising olefinic hydrocarbon products and unreacted paraffinic hydrocarbons.

One of the more specific embodiments relates to a catalytic dehydrogenation process which comprises the steps of (a) heat exchanging an isobutane feed stream with a net hydrogen product stream and a net hydrocarbon product stream chilled in accordance with step (g); (b) further cooling said isobutane feed stream on combination with a hydrogen recycle stream chilled in accordance with step (g) and recycled in accordance with step (h); (c) heating the combined hydrogen/isobutane stream by indirect heat exchange with a reaction zone effluent stream compressed in accordance with step (e); (d) contacting the heated combined stream with a dehydrogenation catalyst in a reaction zone at dehydrogenation conditions including a temperature of from about 1000° to about 1200° F. and a pressure of from about 10 to about 30 psig, to produce a reaction zone effluent stream comprising hydrogen, isobutylene and unreacted isobutane; (e) compressing said effluent stream to a pressure of from about 110 to about 160 psig and cooling said stream to a temperature of from about −20° to about −40° F. in indirect heat exchange with the combined stream in accordance with step (c) and forming a liquid hydrocarbon phase and a hydrogen-rich vapor phase; (f) separating the thus cooled liquid hydrocarbon phase; (g) expanding the hydrogen-rich vapor phase to reduce the pressure thereof to from about 30 to about 50 psig and the temperature to from about −80° to about −90° F. to effect condensation of a residual hydrocarbon phase therefrom; (h) combining one portion of the thus chilled vapor phase with the isobutane feed stream as recycle hydrogen in accordance with step (b); (i) heat exchanging the remaining portion of the chilled hydrogen-rich vapor phase with the isobutane feed stream in accordance with step (a) and thereafter recovering said vapor phase as a net hydrogen product stream; (j) combining the cooled liquid hydrocarbon phase from step (f) and the chilled residual hydrocarbon phase from step (g), heat exchanging the combined hydrocarbon stream with the hydrocarbon feed stream in accordance with step (a), and thereafter recovering the combined stream as a net hydrocarbon products stream comprising olefinic hydrocarbon products stream comprising olefinic hydrocarbon products and unreacted paraffinic hydrocarbons.

Other objects and embodiments of this invention will become apparent in the following detailed specification.

The catalytic dehydrogenation process herein contemplated will preferably utilize a catalytic composite comprising a platinum group metal component, a tin component, and an alkali metal component composited with a porous, high surface area, adsorbent support or carrier material. Of the platinum group metals, i.e., platinum, palladium, ruthenium, rhodium, osmium and iridium, platinum is a preferred catalyst component. The platinum component will generally comprise from about 0.01 to about 2.0 wt.% of the catalytic composite, and the tin component will generally comprise from about 0.01 to about 5 wt.% thereof. Of the alkali metals, i.e., cesium, rubidium, potassium, sodium and lithium, lithium and/or potassium are preferred. The alkali metal will generally constitute from about 0.1 to about 3.5 wt.% of the catalytic composite. One preferred catalytic composite comprises from about 0.1 to about 1.0 wt.% platinum, from about 0.1 to about 1.0 wt.% tin and from about 0.2 to about 1.5 wt.% lithium or potassium composited with a porous adsorbent support or carrier material having a surface area of from about 25 to about 500 m²/g.

Suitable high surface area adsorbent materials for use as a catalyst support or carrier materials include the various charcoals produced by the destructive distillation of wood, peat, lignite, nutshells, bones and other carbonaceous matter, and preferably such charcoals as have been heat treated, or chemically treated, or both, to form a highly porous particle structure of increased adsorbent capacity, and generally defined as activated carbon. Said adsorbent materials also include the naturally occurring clays and silicates, for example, diatomaceous earth, fuller's earth, kieselguhr, attapulgus clay, feldspar, montmorillonite, halloysite, kaolin, and the like, and also the naturally occurring or synthetically prepared refractory inorganic oxides such as alumina, silica, zirconia, etc., or combinations thereof like silica-alumina, silica-zirconia, alumina-zirconia and the like. The preferred carrier materials are the refractory inorganic oxides with best results being obtained with an alumina support or carrier material.

The reaction zone of the present invention preferably comprises at least one radial flow reactor through which the catalytic composite gravitates downwardly to allow a substantially continuous replacement of the catalyst with fresh and/or regenerated catalyst. A detailed description of the moving bed reactors herein contemplated may be obtained by reference to U.S. Pat. No. 3,978,150. With regard to the moving bed type of operation, a particularly preferred form of alumina is the sphere, especially alumina spheres prepared substantially in accordance with the oil-drop method described in U.S. Pat. No. 2,620,314. Briefly, said method comprises dispersing droplets of an alumina sol in a hot oil bath. The droplets are retained in the oil bath until they set into firm gel spheroids. The spheroids are continuously separated from the bath and subjected to specific aging treatments to promote certain desirable properties. The spheres are subsequently dried and calcined to develop pore characteristics and high surface area.

The dehydrogenation reaction is a highly endothermic reaction which is typically effected at near atmospheric pressure conditions. The precise dehydrogenation conditions employed in the dehydrogenation reaction zone will depend on a variety of factors including the composition of the paraffinic hydrocarbon feedstock, the activity of the selected catalyst, and the hydrocarbon conversion rate. In general, dehydrogenation conditions include a pressure of from about 0 to about 35 psig and a temperature of from about 900° to about 1300° F. The paraffinic hydrocarbon feedstock is suitably charged to the reaction zone and contacted with the catalyst contained therein at a liquid hourly space velocity of from about 1 to about 10. Hydrogen, principally recycle hydrogen, is suitably admixed with the hydrocarbon feedstock in a mole ratio of from about 1 to about 10. Preferred dehydrogenation conditions, particularly with respect to $C_3$-$C_4$ paraffinic hydrocarbon feedstocks, include a pressure of from about 10 to about 30 psig and a temperature of from about 1000° to about 1200° F., a liquid hourly space velocity of from about 2 to about 6, and a hydrogen/hydrocarbon mole ratio of from about 2 to about 4.

Pursuant to the process of the present invention, the effluent from the dehydrogenation reaction zone is initially compressed and cooled to form a liquid phase comprising olefinic and paraffinic hydrocarbons and a hydrogen-rich vapor phase. This initial separation is suitably effected at a pressure of from about 85 to about 185 psig in conjunction with a temperature of from about −10° to about −50° F. Preferably, said effluent is initially compressed to a pressure of from about 110 to about 160 psig and cooled to a temperature of from about −20° to about −40° F. in the described manner. In the subsequent further purification of that portion of the hydrogen-rich vapor phase intended for recycle to the dehydrogenation reaction zone, said vapor phase is expanded, for example, by means of a turbo expander, to a pressure which is in excess of the dehydrogenation reaction zone pressure to facilitate the recycle process but generally not in excess of about 65 psig—say from about 15 to about 65 psig—to effect a temperature of from about −75° to about −95° F. Preferably said vapor phase is expanded to a pressure of from about 30 to about 50 psig to lower the temperature thereof to from about −80° to about −90° F.

The further description of the process of this invention is presented with reference to the attached schematic drawing. The drawing represents one preferred embodiment of the invention and is not intended as an undue limitation on the generally broad scope of the invention as set out in the appended claims. Only those compressors, heaters, heat exchangers, coolers and valves are shown that are useful in the description of the process. The utilization of other miscellaneous hardware such as pumps, instrumentation and controls have been omitted as not essential to a clear understanding of the process, the use of such hardware being well within the purview of one skilled in the art.

Referring then to the drawing, a hydrocarbon feed stream comprising isobutane is charged to the dehydrogenation process from a deisobutanizer column which is not shown. The feed stream is introduced by way of line 1 at a temperature of about 90° F. and at a pressure of about 100 psig, and the feed stream is then processed through a heat exchanger 2 to effect an indirect heat exchange with a hydrogen-rich vapor stream passing through line 37 at a temperature of about −87° F. and originating as hereinafter described. The feed stream, thus cooled to about 75° F., is continued through line 1 to a heat exchanger 3 to effect an indirect heat exchange with a liquid hydrocarbon stream passing through line 55 at a temperature of about −33° F., said hydrocarbon stream being derived from a flash drum 51 as hereinafter described. The feed stream, further cooled to a temperature of about 6° F., is then combined with a hydrogen-rich recycle stream from line 38 to provide a combined stream having a hydrogen/hydrocarbon mole ratio of about 2:1, said recycle stream having a temperature of about −87° F. and originating as hereinafter described. The combined stream is then transferred through line 4 to a first heat exchanger 5 wherein the combind stream is increased in temperature to about 64° F., and then to a second heat exchanger 6 wherein the temperature is further increased to about 1074° F. In the first heat exchanger 5, the combined stream is heated by indirect heat exchange with a dried reaction zone effluent stream recovered from a dryer 15 and passing through line 27 at a temperature of about 75° F., and in the second heat exchanger 6, the combined stream is further heated by indirect heat exchange with a reaction zone effluent stream recovered through line 11 at a temperature of about 1134° F. Further heating of the combined stream is accomplished by means of a heater 7 to provide a reactor inlet temperature of about 1190° F., the pressure at this stage having been reduced to about 25 psig due to pressure drop through the system.

The dehydrogenation reactor 8 preferably comprises multiple stacked reaction zones, and the combined stream is processed serially through said zones each of which contains a particulate catalyst disposed as an annular-form bed movable downwardly through said zones. The combined stream is processed downwardly through said annular-form beds at a liquid hourly space velocity of about 4. The combined stream is then processed through said annular-form beds in a substantially radial flow and, since the dehydrogenation reaction is endothermic in nature, intermediate heating of the reactant stream between zones is the preferred practice. The moving catalyst bed permits a continuous addition of fresh and/or regenerated catalyst through conduit 9, and the withdrawal of spent catalyst through conduit 10. The moving bed system herein contemplated is illustrated in U.S. Pat. No. 3,647,680 in conjunction with a continuous catalyst regeneration system, and in U.S. Pat. No. 3,978,150 with reference to the dehydrogenation of paraffinic hydrocarbons.

In any case, the hot (1134° F.) effluent stream from the dehydrogenation reactor 8 is recovered through line 11 and the previously mentioned heat exchanger 6. The reactor effluent stream, reduced in temperature to about 180° F., is then combined with a hydrogen-rich recycle stream from line 53, the source of said stream being a hereinafter described flash drum 51. The reactor effluent stream in combination with said recycle stream is passed through line 12 and compressed and cooled to about 155 psig and 100° F. by a compressor means 13 and a cooling means 14. In practice, said pressure is more conveniently increased in stages with provision for interstage cooling to counter the heat of compression. However, in the interest of simplicity, only one compressor and cooling means is shown.

Vessels 15 and 16 are dryers, each of which contains a desiccant, for example, a bed of molecular sieves. In the present example, dryer 15 is in operation while dryer 16 is undergoing regeneration. Thus, block valves 17, 18, 19 and 20 are in the open position while block valves 21, 22, 23 and 24 are in the closed position, and the reactor effluent stream from line 12 is routed through block valve 17 and line 25 to the dryer 15. The dried reactor effluent stream is then withdrawn from the dryer 15 via line 26 and open block valve 18 to be recovered in line 27 for transfer to the first gas-liquid separator 28. The dried reactor effluent stream in line 27 is processed through the previously mentioned heat exchangers 29 and 5 enroute to the first gas-liquid separator 28. In the first mentioned heat exchanger 29, the dried reactor effluent stream in line 27 is heat exchanged with a hereinafter described liquid hydrocarbon stream passing through line 55 at a temperature of about −42° F.; and in the second heat exchanger 5, the dried stream is further heat exchanged with the heretofore described combined stream passing through line 4 at a temperature of about −49° F. The cumulative affect is a dried reactor effluent stream for introduction into the first gas-liquid separator 28 at a temperature of about −28° F. and at a pressure of about 135 psig.

The hydrogen-rich vapor phase that forms in the first gas-liquid separator 28 at said conditions of temperature and pressure is recovered by way of an overhead line 30. One portion of said vapor phase is diverted through line 40 for use in the dryer 16 as hereinafter described, and the remainder is transferred through line 31 to a turbo expander 32 wherein said vapor phase is reduced in pressure to about 41 psig with a resulting reduction in temperature to about −87° F. The hydrogen-rich vapor phase thus chilled is transferred via line 33 to a second gas-liquid separator 34 wherein a resulting liquid phase comprising residual hydrocarbons settles out to be recovered through line 35. The hydrogen-rich vapor phase is recovered from the second gas-liquid separator 34 through an overhead line 36 at said temperature and pressure, and one portion thereof, substantially equivalent to the net hydrogen product, is diverted through line 37 and the previously mentioned heat exchanger 2. The balance of the hydrogen-rich vapor stream from line 36 is diverted into line 38 to be combined with the feed stream introduced to the process by way of line 1 as has been previously described, said portion being thus recycled to the reactor 8 in admixture with said feed stream via line 4.

That portion of the hydrogen-rich vapor phase recovered overhead from the second gas-liquid separator 34 and diverted through line 37 as net hydrogen, is discharged from the process by way of line 39 in admixture with a hydrogen-rich vapor stream from line 47. This last mentioned vapor stream results from regeneration of the desiccant in the dryer 16. In the regeneration process, a portion of the hydrogen-rich vapor phase recovered from the first gas-liquid separator 28 is diverted through line 40, heated in a heater 41, and then circulated over the desiccant. The vapor stream enters the dryer 16 by way of line 40, an open block valve 19 and line 42. The water-containing vapor stream, recovered by way of line 43, an open block valve 20 and line 44, enters a knock-out pot 45 wherein water is allowed to settle out for discharge through line 46. The hydrogen-rich vapor phase recovered through line 47 is then recombined with the net hydrogen stream from line 37 and discharged by way of line 39.

The liquid hydrocarbon phase that settles out in the second gas-liquid separator 34 is recovered through line 35 and a pressure reducing valve 48 and combined with the liquid hydrocarbon phase that settles out in the first gas-liquid separator 28, the latter being recovered through line 49 and a pressure reducing valve 50. The combined stream is then introduced into a flash drum 51 by way of line 52 at a temperature of about −33° and at a pressure of about 10 psig. Residual hydrogen is flashed from the liquid hydrocarbon phase and recovered in an overhead line 53 to be combined with the reaction zone effluent stream from line 11 for eventual recycle to the gas-liquid separator 28. The liquid phase recovered from the bottom of the flash drum 51 is increased in pressure by means of pump 54 to about 384 psig and passed through line 55 at a temperature of about −33° F. to the previously mentioned heat exchanger 3 wherein the stream is heated to about −42° F. in indirect heat exchange with the feed stream in line 1. The hydrocarbon stream is further heated to about 75° F. in indirect heat exchange with the dried reaction zone effluent stream in heat exchanger 29, and said stream is then continued through line 55 at a pressure of about 384 psig for further treatment in conventional product recovery means which are not shown.

The refrigeration energy required herein is derived from the effluent compressor 13 via expansion of the compressed effluent stream across the turbo expander 32, the effluent stream thus serving as a refrigerant stream. The heat exchanger combination depicted in the drawing is designed to minimize the required refrigeration energy, and to maximize the recovery of that energy which is expended. In the latter case, this is accomplished by heat exchanging both the net gas (line 37) and net liquid (line 55) product streams with the inlet feed stream passing through line 1. To minimize the energy required for refrigeration, it is necessary to minimize the pressure drop from the effluent compressor 13 to the high pressure separator 28 whereby a maximum expansion of the refrigerant effluent stream across the turbo expander 32, and therefore maximum cooling, is realized, said pressure drop being largely due to heat exchanger back pressure. By the unique device of heat exchanging the net gas and the net liquid product streams with the inlet feed stream, as opposed to the more obvious expedient of heat exchanging said product streams with the refrigerant effluent stream flowing through line 27, heat exchanger back pressure in said effluent stream is reduced to maximize the cooling effect of the turbo expander 32 in the manner heretofore stated.

The following data illustrates the composition of certain relevant streams which comprise the process of the above example representing one preferred embodiment of this invention.

| | Line No. | | | | | | | | | |
|---|---|---|---|---|---|---|---|---|---|---|
| | 1 | 4 | 11 | 27 | 31 | 36 | 38 | 49 | 52 | 55 |
| Component, lb-mols/hr | | | | | | | | | | |
| hydrogen | 0.00 | 7,322.28 | 8,640.44 | 8,660.25 | 8,639.24 | 8,638.73 | 7,322.28 | 21.00 | 21.51 | 1.70 |
| methane | 0.00 | 673.76 | 822.85 | 837.30 | 796.78 | 794.90 | 673.76 | 40.52 | 42.40 | 27.95 |
| ethane | 0.00 | 68.48 | 114.34 | 116.46 | 83.43 | 80.80 | 68.48 | 33.03 | 35.66 | 33.55 |
| propene | 0.00 | 17.06 | 70.67 | 71.32 | 24.95 | 20.13 | 17.06 | 46.37 | 51.19 | 50.54 |
| propane | 54.44 | 93.67 | 199.72 | 201.29 | 60.75 | 46.28 | 39.23 | 140.53 | 155.00 | 153.44 |
| isobutene | 0.00 | 32.79 | 1,334.57 | 1,337.45 | 119.41 | 38.69 | 32.79 | 1,218.04 | 1,298.76 | 1,295.88 |
| 1-butene | 0.00 | 0.18 | 7.75 | 7.77 | 0.68 | 0.21 | 0.18 | 7.09 | 7.55 | 7.54 |
| 2-butene | 0.00 | 0.15 | 15.31 | 15.33 | 0.85 | 0.17 | 0.15 | 14.47 | 15.15 | 15.13 |
| butadiene | 0.00 | 0.02 | 1.25 | 1.26 | 0.10 | 0.03 | 0.02 | 1.16 | 1.23 | 1.23 |
| isobutane | 3,478.56 | 3,556.39 | 2,078.00 | 2,083.61 | 230.52 | 91.82 | 77.83 | 1,853.09 | 1,991.79 | 1,986.18 |
| n-butane | 70.99 | 71.61 | 40.42 | 40.48 | 2.82 | 0.73 | 0.62 | 37.66 | 39.76 | 39.69 |
| Total | 3,603.99 | 11,836.38 | 13,325.31 | 13,372.49 | 9,959.52 | 9,712.46 | 8,232.39 | 3,412.97 | 3,660.01 | 3,612.82 |
| lbs/hr | 208,700 | 245,199 | 245,196 | 246,122 | 56,788 | 43,057 | 36,496 | 189,333 | 203,064 | 202,138 |
| mol. wt. | 57.91 | 20.7 | 18.4 | 18.4 | 5.7 | 4.43 | 4.43 | 55.47 | 55.48 | 55.95 |
| b.p.s.d. | 25,415.5 | 0.0 | 0.0 | — | 0.0 | 0.0 | 0.0 | 22,762 | — | 24,252 |
| $10^6$ s.c.f.d. | 0.0 | 107.80 | 121.37 | — | 90.71 | 88.46 | 74.98 | 0.0 | — | 0.0 |

In the practice of the present invention, a significant improvement in the separation of recycle hydrogen from a total reaction zone effluent, comprising normally gaseous olefinic as well as paraffinic hydrocarbons, is effected at relatively mild conditions of temperature and pressure. Recycle hydrogen is recovered substantially free of said olefinic hydrocarbons to maximize the $C_3$-$C_4$ paraffinic hydrocarbon conversion in the dehydrogenation zone in accordance with the aforesaid equilibrium reaction conditions.

We claim as our invention:

1. A catalytic dehydrogenation process which comprises the steps of:
   (a) heat exchanging a $C_2+$ normally gaseous paraffinic hydrocarbon feed stream with a net hydrogen product stream and a net hydrocarbon product stream chilled in accordance with step (g);

(b) further cooling said hydrocarbon feed stream by admixture with a hydrogen recycle stream chilled in accordance with step (g) and recycled in accordance with step (h);

(c) heating the combined hydrogen/hydrocarbon stream by indirect heat exchange with a reaction zone effluent stream compressed in accordance with step (e);

(d) contacting the heated combined stream with a dehydrogenation catalyst in a reaction zone at dehydrogenation conditions producing a reaction zone effluent stream comprising hydrogen, olefinic hydrocarbon product and unreacted paraffinic hydrocarbons;

(e) compressing said effluent stream and cooling the same by indirect heat exchange with the combined stream in accordance with step (c) and forming a liquid hydrocarbon phase and a hydrogen-rich vapor phase;

(f) separating the thus cooled liquid hydrocarbon phase;

(g) expanding the hydrogen-rich vapor phase to effect a further chilling and condensation of a residual hydrocarbon phase therefrom;

(h) combining one portion of the chilled vapor phase with the hydrocarbon feed stream as recycle hydrogen in accordance with step (b);

(i) heat exchanging the remaining portion of the chilled hydrogen-rich vapor phase with the hydrocarbon feed stream in accordance with step (a) and thereafter recovering said vapor phase as a net hydrogen product stream;

(j) combining the cooled liquid hydrocarbon phase from step (f) and the chilled residual hydrocarbon phase from step (g), heat exchanging the combined hydrocarbon stream with the hydrocarbon feed stream in accordance with step (a), and thereafter recovering the combined stream as a net hydrocarbon products stream comprising olefinic hydrocarbon products stream comprising olefinic hydrocarbon products and unreacted paraffinic hydrocarbons.

2. The process of claim 1 further characterized with respect to step (a) in that said hydrocarbon feed stream comprises $C_3$–$C_4$ paraffinic hydrocarbons.

3. The process of claim 1 further characterized with respect to step (a) in that said hydrocarbon feed stream comprises isobutane.

4. The process of claim 1 further characterized with respect to step (d) in that said dehydrogenation conditions include a temperature of from about 900° to about 1300° F. and a pressure of from about 0 to about 35 psig.

5. The process of claim 1 further characterized with respect to step (d) in that said dehydrogenation conditions include a temperature of from about 1000° to about 1200° F. and a pressure of from about 10 to about 30 psig.

6. The process of claim 1 further characterized with respect to step (e) in that said effluent stream is compressed to a pressure of from about 85 to about 185 psig and cooled to a temperature of from about $-10°$ to about $-50°$ F.

7. The process of claim 1 further characterized with respect to step (e) in that said effluent stream is compressed to a pressure of from about 110 to about 160 psig and cooled to a temperature of from about $-20°$ to about $-40°$ F.

8. The process of claim 1 further characterized with respect to step (g) in that said vapor phase is expanded to reduce the pressure thereof to from about 15 to about 65 psig, and the temperature to from about $-75°$ to about $-95°$ F.

9. The process of claim 1 further characterized with respect to step (g) in that said vapor phase is expanded to reduce the pressure thereof to from about 30 to about 50 psig, and the temperature to from about $-80°$ to about $-90°$ F.

* * * * *